United States Patent
Leonardi

(10) Patent No.: US 10,102,926 B1
(45) Date of Patent: Oct. 16, 2018

(54) DETECTING, ANALYZING AND IMPACTING IMPROVEMENT OPPORTUNITIES RELATED TO TOTAL COST OF CARE, CLINICAL QUALITY AND REVENUE INTEGRITY

(71) Applicant: Sentry Data Systems, Inc., Deerfield Beach, FL (US)

(72) Inventor: Travis Leonardi, Deerfield Beach, FL (US)

(73) Assignee: SENTRY DATA SYSTEMS, INC., Deerfield Beach, FL (US)

( * ) Notice: Subject to any disclaimer, the term of this patent is extended or adjusted under 35 U.S.C. 154(b) by 424 days.

(21) Appl. No.: 14/882,928

(22) Filed: Oct. 14, 2015

Related U.S. Application Data

(60) Provisional application No. 62/063,776, filed on Oct. 14, 2014.

(51) Int. Cl.
  *G06N 7/00* (2006.01)
  *G16H 50/20* (2018.01)
  *G06F 19/00* (2018.01)

(52) U.S. Cl.
  CPC ......... *G16H 50/20* (2018.01); *G06F 19/3468* (2013.01); *G06F 19/3481* (2013.01); *G06N 7/00* (2013.01)

(58) Field of Classification Search
  None
  See application file for complete search history.

(56) References Cited

U.S. PATENT DOCUMENTS

| | | | |
|---|---|---|---|
| 7,811,279 B2 * | 10/2010 | John | A61M 5/172 604/890.1 |
| 2011/0054935 A1 | 3/2011 | Hardaway | |
| 2015/0278924 A1 | 10/2015 | Maurer | |

OTHER PUBLICATIONS

"GPs' Diagnostic Skills Could Be Obsolete Within 20 Years' Time, Says Hunt," Alex Matthews-King, Pulse Today, Oct. 6, 2015 (2 pages).
Sample 340B Policy & Procedures Manual, Feb. 2014, Apexus, pp. 1-18.

* cited by examiner

*Primary Examiner* — Wilbert L Starks
(74) *Attorney, Agent, or Firm* — Loeb & Loeb LLP

(57) ABSTRACT

Example embodiments of a system, apparatus, computer readable media, and method are disclosed for improving clinical and financial outcomes for a healthcare provider The example embodiments may be used for aggregating data corresponding to care for a group of patients by at least one healthcare provider, generating a statistical model based on the aggregated data, periodically determining a current value for the treatment parameter associated with care of a patient provided by a healthcare provider, and causing treatment to be administered to the patient in response to applying the statistical model to determine that the current value for the treatment parameter is associated with an adverse outcome.

20 Claims, 6 Drawing Sheets

DETECTING, ANALYZING AND IMPACTING IMPROVEMENT OPPORTUNITIES RELATED TO TOTAL COST OF CARE, CLINICAL QUALITY AND REVENUE INTEGRITY

CROSS REFERENCE TO RELATED APPLICATIONS

This application claims the benefit of, and priority to, U.S. Prov. Appl. No. 62/063,776 filed Oct. 14, 2014, entitled "Detecting, Analyzing And Impacting Improvement Opportunities Related To Total Cost Of Care, Clinical Quality And Revenue Integrity," the entire content of which is incorporated herein by reference.

BACKGROUND

Field of the Invention

The invention relates to facilitating management of healthcare providers. Among other fields and applications, the invention has utility in detecting, analyzing and impacting improvement opportunities related to total cost of care, clinical quality and revenue integrity.

Description of Related Art

Hospitals across the country are challenged with optimally managing their financial performance while simultaneously improving the quality of care and outcomes of their patient population. Existing technologies do not satisfactorily address these issues.

BRIEF SUMMARY

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

Example embodiments of a system, apparatus, computer readable media, and method are disclosed for improving clinical and financial outcomes for a healthcare provider Specifically, the example embodiments may be used for aggregating data corresponding to care for a group of patients by at least one healthcare provider, generating a statistical model based on the aggregated data, periodically determining a current value for the treatment parameter associated with care of a patient provided by a healthcare provider, and causing treatment to be administered to the patient in response to applying the statistical model to determine that the current value for the treatment parameter is associated with an adverse outcome.

BRIEF DESCRIPTION OF THE DRAWINGS

The invention may be better understood by references to the detailed description when considered in connection with the accompanying drawings. The components in the figures are not necessarily to scale, emphasis instead being placed upon illustrating the principles of the invention. In the figures, like reference numerals designate corresponding parts throughout the different views.

Figure 1:
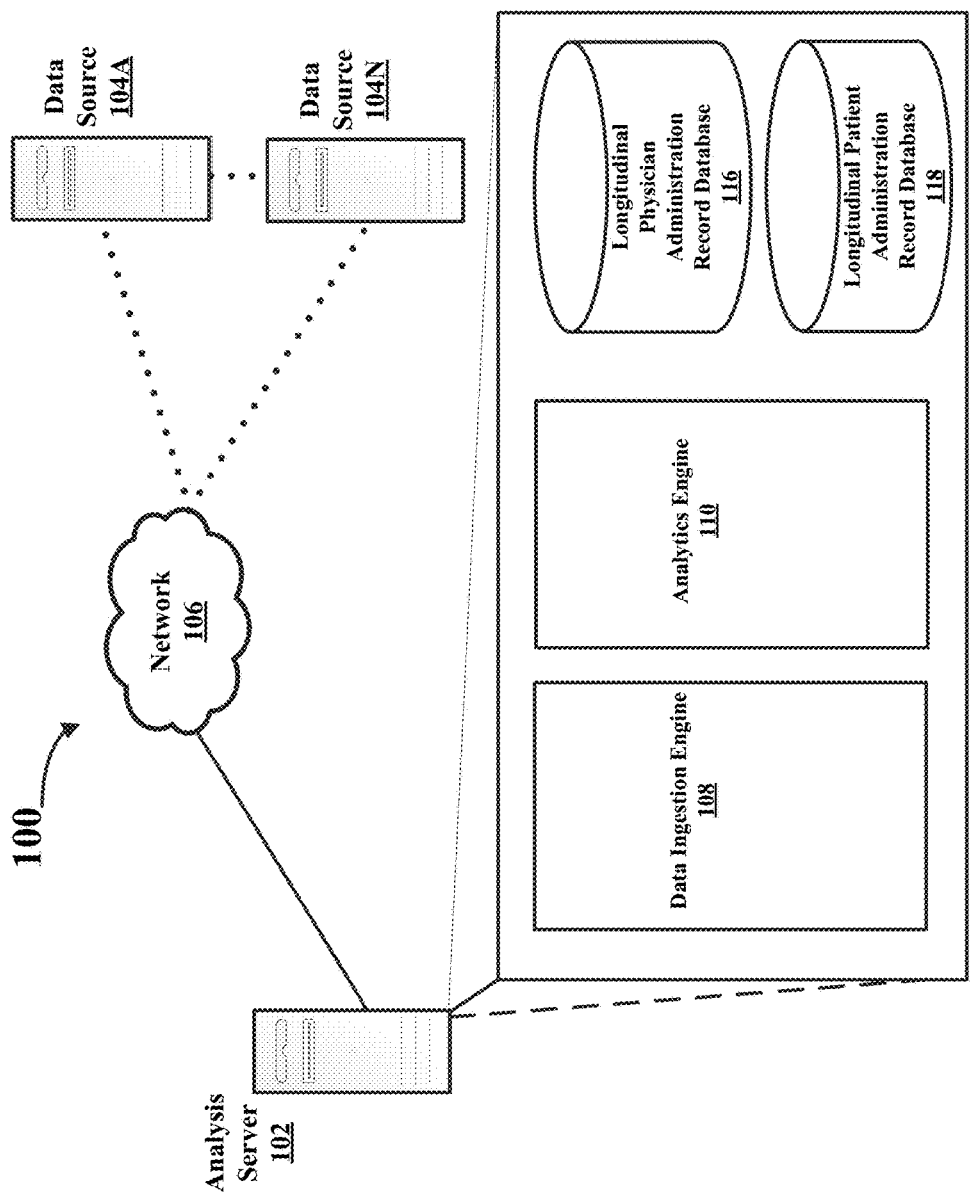
FIG. 1 illustrates a system in accordance with example embodiments.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

DETAILED DESCRIPTION

The present invention now will be described more fully with reference to the accompanying drawings, which form a part hereof, and which show, by way of illustration, specific exemplary embodiments by which the invention may be practiced. These illustrations and exemplary embodiments are presented with the understanding that the present disclosure is an exemplification of the principles of one or more inventions and is not intended to limit any one of the inventions to the embodiments illustrated. The invention may be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods, systems, computer readable media, apparatuses, or devices. Accordingly, the present invention may take the form of an entirely hardware embodiment, an entirely software embodiment, or an embodiment combining software and hardware aspects. The following detailed description is, therefore, not to be taken in a limiting sense.

Hospitals and other healthcare providers have long struggled with accurately identifying and managing their costs and revenue opportunities, particularly at a patient, contract, procedure, and physician level across major cost centers. Existing technologies fail to identify and account total costs and net revenues at the patient encounter level, and instead can only use approximations derived from a set of clinical and operational assumptions. Conventional solutions for identifying cost savings and revenue opportunities, along with specific actionable areas for improvement in the quality of patient care and outcomes, are problematic. Existing solutions fail to identify and allocate both total provider cost of care and profitability at a patient encounter level, in near real-time, using multiple bi-directional electronic hospital and patient medical records data.

To overcome these and other deficiencies, the example embodiments connect disparate data pertaining to cost, quality, and reimbursement outcomes, and then provide robust, highly configurable, and intuitive analytics and reporting capabilities tailored to reducing variability within a healthcare delivery system for targeted improvements in both care quality and profitability. The example embodiments assist hospitals and other healthcare organizations to accurately determine the costs and operating margin (profit/loss) related to the provision of services and to offer actionable opportunities for improving both operating margin and patient outcomes.

The example embodiments further identify supply chain and revenue enhancement errors that result in foregone savings and/or revenue opportunities for the hospital. The example embodiments enable efficient correction of these errors via multiple rules-driven work queues that are enhanced through the use of bi-directional data feeds to automatically provide corrections back to the various hospital host information systems. In a bi-directional system integration, data is able to pass from one or more hospital information systems (e.g., an electronic medical record system, charge master or item master, materials management information system, etc.) into a secondary system for additional work or manipulation of the data; and subsequently the secondary system passes the new or revised data into the one or more hospital information systems. The example embodiments attempt to ensure data continuity across disparate systems and may also reduce or even eliminate the need for redundant manual system documentation by staff— ultimately yielding a more efficient overall process.

The example embodiments may further facilitate healthcare providers' compliance with healthcare reforms at the Federal and local levels, and may account for changing reimbursement relationships among various healthcare organizations. To address these issues, the example embodiments provide automated systems that give timely, detailed and accurate information related to the costs of care and related third party reimbursements, and account for patients covered under risk-sharing or bundled payment arrangements.

FIG. 1 illustrates a system 100 in accordance with example embodiments. The system 100 may provide for collecting, aggregating, and analyzing data from operational, clinical and financial areas of a hospital to identify cost savings, revenue enhancement, and patient care outcomes opportunities.

As depicted, system 100 may include an analysis server 102 communicatively coupled to one or more data source servers 104A-N via network 106. Data source servers 104A-N may communicate data to analysis server 102 about expenses incurred by a hospital or other healthcare provider during treatment of its patients. Types of data sources may include hospital systems, wholesalers, distributors, suppliers, pharmacies, and the like. The data may include information on expenditures for medications or supplies purchased by the hospital, labor charges, real estate charges, and the like.

The analysis server 102 may include a number of engines for processing the data, including a data ingestion engine 108 and an analytics engine 110, as well as databases 116 and 118 respectively storing patient and physician longitudinal administration records (LARs). Each engine described herein may be a discrete piece of hardware hard coded to perform the functions described herein. In other examples, the functions of an engine may be implemented in software as computer readable instructions stored in memory whereby execution of the computer readable instructions by at least one processor cause the at least one processor, or at least one computer, server, or other device, to perform the functions described herein. In yet other examples, any of the engines and functions described herein may be implemented as discrete pieces of hardware and others may be implemented in software. In other examples, an engine may include at least one processor and at least one memory storing computer executable instructions that, when executed by the at least one processor, cause the at least one processor, computer, server, or other device, to perform the functions described herein. In further examples, some functions performed by an engine may be implemented as one or more discrete pieces of hardware and other functions may be implemented in software.

Figure 2:
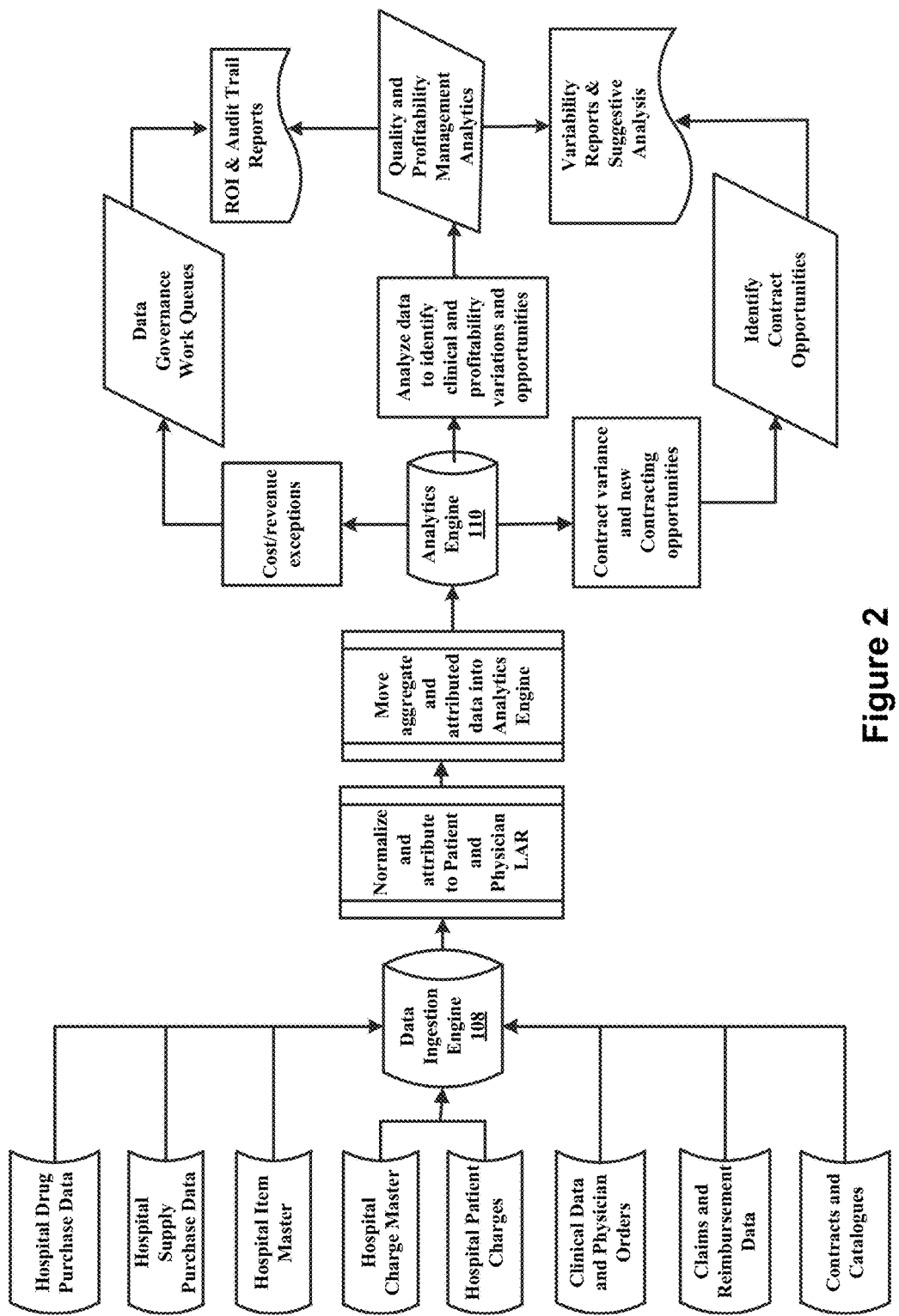
FIG. 2 illustrates a flow diagram of a process for detecting, analyzing and impacting improvement opportunities related to total cost of care, clinical quality and revenue integrity in accordance to example embodiments.

FIG. 2 illustrates a flow diagram of a process implemented by system 100 for detecting, analyzing and impacting improvement opportunities related to total cost of care, clinical quality and revenue integrity in accordance to example embodiments. As depicted, a data ingestion engine 108 may obtain multiple disparate data feeds from a variety of data source servers 104A-N (e.g., client and client vendor host server systems). For example, the data ingestion engine 108 may receive data feeds via HL7 transmission or periodically in flat file batches (e.g., once a day). Examples of data types include hospital drug purchase data, hospital supply purchase data, hospital item master data, hospital charge master data, hospital patient charges data, clinical data, physician orders data, claims data, reimbursement data, contracts data, and catalogues data.

Other types of data may include master data sets, Electronic Medical Records, Physician Order Entry data, financial and cost accounting files, and Admit, discharge, transfer (ADT) data. Master data sets (e.g., Item, Charge, Contract) may be used in a data connection crosswalk to the LAR, for validation, and verification for data governance workflows. In a data connection crosswalk, the data ingestion engine 108 may apply an algorithm to identify common data elements across multiple files with source data from multiple data source servers 104A-N. The data ingestion engine 108 may link together information from these disparate files via the process of first linking common data elements in such a way as to provide at least some assurance that linked information is actually related. In an example, the data ingestion engine 108 may create a roadmap to navigate through large amounts of data to connect "Point A" to "Point Z". For example, in a hospital setting, supply purchase prices, physician orders, patient charges, and insurance company payments may each be recorded in a different software system. Through the use of the data connection crosswalk, the data ingestion engine 108 may connect these elements back to the individual patients using available common attributes to provide hospital management information on total utilization, cost, and profitability impact of that episode of care.

Electronic Medical Record data may be used for documented utilization and quality/outcomes attributes related to episodic patient care. Physician Order Entry data may be used for documented utilization and quality/outcomes attributes related to episodic patient care, as well as to drive suggestive analytics and proactive potential event alert functionality (e.g., statistical analysis and corresponding clinical alerts for probable Catheter Acquired Urinary Tract Infection (CAUTI) based on calculated "days with catheter" metric using time stamps from when doctor starts and discontinues orders). Purchase transaction files may be used for determining the total supply cost attributable to a patient based on the actual care they received, identifying nonvalue-added variability trends in both procurement and utilization, and for evaluating performance and compliance against established supplier and group purchasing organization contracts.

Financial and cost accounting files (Labor, Capital, etc.) may be used for determining total cost of patient episodic care. Admit, discharge, transfer (ADT) data may be used for determining patient location, system throughput and appropriate cost allocations based on time and activity tracking. Other relevant data sets as deemed necessary based on client environment and continued system development/feature enhancements may also be used.

The ingestion engine 108 may ingest the data and leverage Drug and Supply Formulary Matrices to appropriately allocate costs to the Patient and Physician longitudinal administration records (LARs) based on actual utilization and purchase history. A patient LAR is a database record of patient medical histories including diagnoses, treatments, service locations, service dates, service providers and related financial, clinical and demographic information. A physician LAR is a database record of physicians including credentialing information, hospital admitting privileges and related demographic, educational and practice information.

Using the matrices, the ingestion engine 108 may employ a series of data connection crosswalks to connect actual purchase price information from procurement files (e.g., invoice records) to the actual patient in the LAR, based on documented utilization across several systems, including patient charges, physician orders, surgical logs, etc. For example, the ingestion engine 108 may allocate the actual supply and its associated true acquisition cost directly to the patient who received it. The ingestion engine 108 may perform the allocation in near real time as the data becomes available and this allocation may be significantly more accurate and timely than the existing cost allocation methods available in the market today. In contrast, traditional cost accounting methods rely on a set of assumptions to allocate approximate costs to a patient—often using an approximation called a relative value unit (RVU)—typically on a monthly or even quarterly basis, and with a single and sometimes even double-digit margin of error.

The ingestion engine 108 may perform normalization as part of data ingestion. The normalization process may provide a consistent format to raw data received from the same or different data sources. For example, different data sources may assign different names to the same product or same supplier of the product. For instance, one data source may refer to a supplier as J&J, whereas another may refer to that supplier as Johnson & Johnson. The ingestion engine 108 may apply a consistent format to refer to the supplier by the same name (e.g., substitute J&J for Johnson & Johnson) across some or all data sources. The ingestion engine 108 may also cleanse the raw data. Cleansing may be the process of one or more of identifying missing data, identifying duplicate data, or identifying errors in the data.

Subsequent to ingesting the data, the ingestion engine 108 may replicate data into the analytics engine 110 for operational, financial and quality-related analytics. Proceeding along the upper right branch of the flow diagram in FIG. 2, the analytics engine may govern data accuracy and synchronization across disparate procurement and revenue systems, including an item master and charge description master data. The item master is a database record that identifies some or all products and services purchased by a hospital and that may be billable to a patient or his/her health insurance plan. The charge description master (CDM) is a code and description associated with financial charges for billable and non-billable healthcare services.

In an example, the analytics engine 110 may establish a data governance foundation by determining relevant data variances and lack of synchronicity between health information systems (HIS) that contribute to both operational and financial efficiency and effectiveness. Conventionally, hospitals may hire consulting companies on recurring basis to clean up the Item Master and CDM files. During the period between these data cleanups, the hospital's Item Master and CDM files will re-accumulate errors and missing information that results in lost savings and/or revenue opportunities. The analytics engine 110 may address these cleanup problems by first providing an exception-based use-case framework that permits authorized users to identify and correct purchase and charge-related issues which are uniquely posted back into the hospital information system through a bi-directional data feed.

In an example, to govern data accuracy and synchronization, the analytics engine 110 may auto-evaluate incoming disparate data feeds to identify "outlier" relationships between dependent data elements within or across client systems. An outlier relationship may be an instance in which one or more data elements do not meet or fall within a specified parameter (e.g., required for optimal performance and results). An example of an outlier relationship is where a purchase price from an invoice does not equal a purchase price listed in the Item Master. Another example may be the existence of a charge code in a master file that is invalid, and would therefore result in a billing error or insurance denial when used. A further example may be an instance in which the purchase price of an item exceeds the charged price, thereby resulting in a negative margin event every time the hospital uses and bills for that specific item.

The analytics engine 110 may assign identified data outliers to stratified user work queues for evaluation, correction, or subsequent action/intervention. A stratified user work queue may be a system-generated end-user worklist, organized by the magnitude of each correction opportunity in descending order. Examples of stratified user work queues include, but are not limited to, a list of specific instances in which purchase cost exceeds charge amount, a list of instances in which package size conversion ratios are incorrect, and/or a list of instances in which the revenue codes being assigned to a patient account are invalid.

Once the analytics engine 110 has established a data governance foundation—which may be the result of the process and functionality detailed in the preceding paragraphs—the analytics engine 110 may use analytics to manage costs, utilization and revenues by patient, procedure, physician, location, service line and third party payer. For example, the analytics engine 110 may employ suggestive and predictive analytics to guide the user toward specific actions or interventions that may be likely to produce a better clinical and/or fiscal result. Predictive analytics may be defined as a variety of statistical techniques including one or more of modeling, machine learning, data mining, and game theory, that analyze current and historical facts to make predictions about future events. Suggestive analytics may rely on combining relevant historical and statistical data into useful information that may then be leveraged by end-users to inform their decision making.

To perform suggestive and predictive analytics, the analytics system 110 may analyze related historical data on transactions and patient-level utilization, and in certain cases may combine that data with statistical analysis or scenario-based modeling to either alert the user to a potential negative-impact scenario, such as a possible readmission, or the increasing probability of a hospital acquired infection (predictive), or to suggest possible courses of action that may yield a better clinical and/or financial outcome (e.g., "In this type of case other surgeons in your hospital used Product X, which costs 10% less than Product Y and also has a 5% lower rate of surgical revision.").

Via graphical user interfaces, the analytics engine 110 may present actionable resolutions and options for correcting issues based on results from the suggestive and predictive analytics. For example, the analytics engine 110 may present to a user automated dashboards for pinpointing specific areas of high clinical variation, high cost variability, and poor profitability to enable rapid drill-down analysis for identifying and confirming root causes of the clinical variation, cost variability, and poor profitability. To calculate high cost variability, for example, the analytics engine 110 may calculate maximum potential return on investment (ROI) based on historical utilization and price/charge rate differentials, then track actual cumulative ROI based on the chosen client resolutions.

The following illustrates an example of how the analytics engine 110 may calculate both a predictive and actual ROI for a specific identified issue in which a product was purchased that is not listed in the hospital's supply formulary, and therefore procurement and utilization are not being actively managed:

Example: Purchased Item Not in Formulary
Step 1: Identify Potential Annual Opportunity
   Source Data:
   Item Purchased Not in Formulary ($Item_n$)
   Quantity Purchased (Q)
   Price Paid (P)
   Time Frame=Most Recent Historical 12 Months
   Example Calculation
   Calculate Cost Basis (CB) where $$CB_h = \text{Current Price of } Item_n(P_c^n) \times \text{Historical Quantity of } Item_n(Q_h^n)$$

Calculate Potential Annual Opportunity (PAO) where $$PAO = CB_h$$

Example Scenario where current cost and utilization are not actively managed $$P_c^n = \$100/\text{Case}$$

$$Q_h^n = 10 \text{ Cases}$$

1. Calculate Cost Basis:

$$CB_h = P_c^n \times Q_h^n$$

$$CB_h = \$100 \times 10$$

$$CB_h = \$1,000$$

2. Calculate Potential Annual Opportunity:

$$PAO = CB_h$$

$$PAO = \$1,000$$

$$PAO = \$1,000$$

Step 2: Identify Actual ROI
   Step 2(a): Calculate Actual Total Cost (ATC)
   Source Data:
     Item Purchased Not in Formulary ($Item_n$)
     Quantity Purchased (Q)
     Therapeutic Equivalents (User Defined)
     Price Paid (P)
     Time Frame=Current Date−Exception Identified Date
   Example Calculation
   Calculate Cost Basis (CB) where $$CB_h = \text{Current Price of } Item_n(P_c^n) \times \text{Current Qnty of } Item_n(Q_c^n)$$

Example Scenario where product price is reduced and utilization decreased $$P_c^n = \$80/\text{Case}$$

$$Q_c^n = 9 \text{ Cases}$$

Calculate Cost Basis:

$$CB_n = P_c^n \times Q_c^n$$

$$CB_n = \$80 \times 10$$

$$CB_n = \$720$$

Step 2(b): Calculate Actual ROI:

$$ROI = CB_h - CB_n$$

$$ROI = \$1,000 - \$720$$

$$ROI = \$280$$

Figure 3:
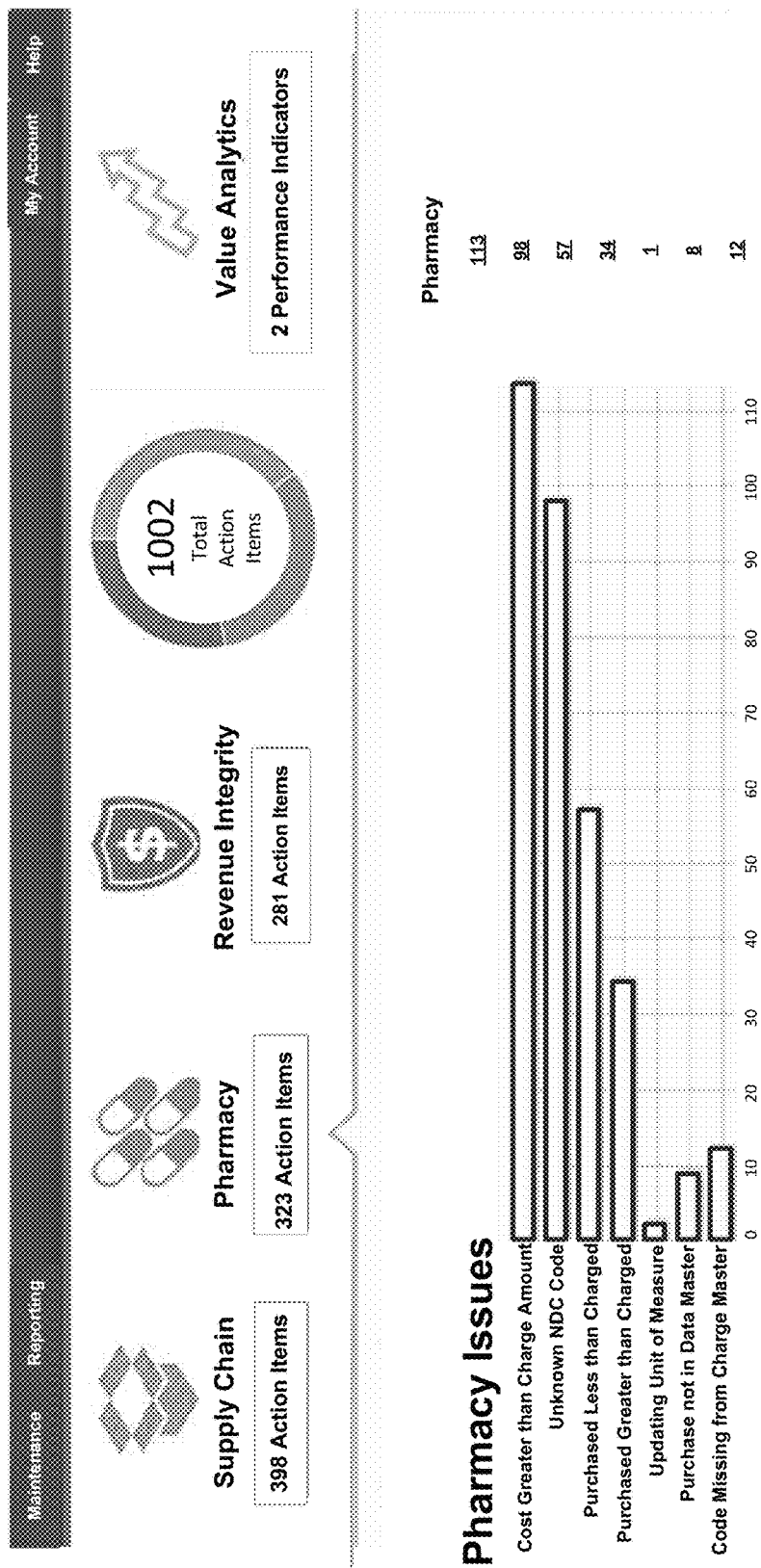
FIGS. 3-5 illustrate example graphical user interfaces in accordance with example embodiments.

FIG. 3 provides an example graphical user interface depicting stratified end user cost containment work queues listing automated system-identified variances in accordance with example embodiments. The depicted GUI lists a total number of action items associated with the hospital's supply chain, pharmacy, and revenue integrated. Example pharmacy issues may include "cost greater than charge amount," "unknown NDC code," "purchased less than charged," "purchased greater than charged," "updating unit of measure," "purchase not in data master," and "code missing from charge master." The GUI also depicts value analytics, which may be selectable graphical links the user can click on to navigate to the more detailed utilization reporting features.

Figure 4:
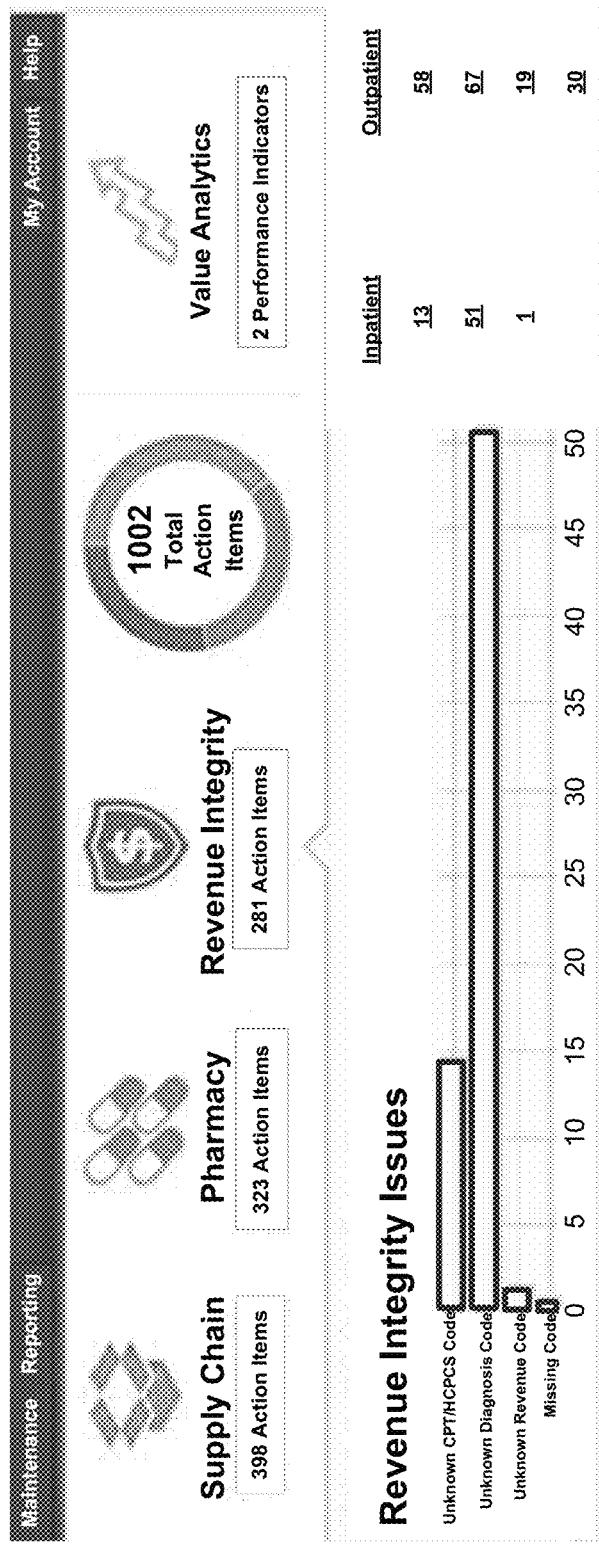

FIG. 4 provides an example graphical user interface depicting stratified end user revenue enhancement work queues listing automated system-identified variances in accordance with example embodiments. The depicted GUI lists revenue integrity issues. Examples of such issues include "unknown CPT/HCPCS code," "unknown diagnosis code," "unknown revenue code," and "missing code."

Referring again to FIG. 2 and proceeding along the middle branch of the flow diagram, the analytics engine 110 may provision patient and physician longitudinal administration records (LARs) to enable quality/profitability analytics. The analytics engine 110 may identify outcomes for specific patient encounters in terms of both operating profitability (margin), contribution margin (fixed cost coverage), and quality (clinical/patient perception).

In an example, the analytics engine 110 may expand databases 116 and/or 118 to include diverse clinical, operational, and financial data. Examples of expanded data sets include non-drug supplies and contracts, third party payer contracts and reimbursement data, finance and accounting system data, and labor data. The analytics engine 110 may use the Drug and Supply formulary Matrices, as described above, to allocate specific costs, care and financial outcomes to specific patients and physicians based on actual utilization (in the case of direct variable costs) as opposed to relative value unit (RVU) or other volume-based allocations.

The analytics engine 110 may also employ time and activity based costing (TABC) derivative algorithms to allocate fixed direct and indirect costs to patients in order to arrive at total cost of care, and then incorporate clinical and revenue data connection points to drive robust profitability and care variance analytic capabilities. The analytics engine 110 may determine total cost of care by first using the data crosswalks in the formulary matrices to assign the direct variable costs of supplies and drugs to the corresponding patient account. The analytics engine 110 may then assign non-labor costs based on combining actual utilization as recorded in the electronic medical records with departmental cost data from the hospital financial system. Finally, the analytics engine 110 may allocate direct and indirect labor costs using a time-based costing approach. The following provides an example:

Example (Simplified Using Fictional Data)

Patient Acct 12345

Supply Cost: Σ(Unit Cost×Volume Utilized)=$3500

Drug Cost: Σ(Unit Cost×Volume Utilized)=$1500

Imaging and Lab: Σ(Unit Cost×Volume Utilized) =1000

Labor Cost (OR): OR Labor Cost=Hourly Comp for Operating Room (OR) staff×OR Time (OR End–OR Start)=5000

Labor Cost (Post-op Care by Location): Labor Cost= (Periodic Caregiver Comp/Periodic All Patient LOS)×Patient Acct 12345 LOS=4000

Total Cost of Patient Care=$15,000

Profitability analysis using the example embodiments may be more robust because once total cost of patient care is determined, the analytics engine 110 may then compare total cost of patient care to actual or anticipated net patient revenue, as determined by existing payer contracted reimbursement. This advancement is indicated by the examples below:

Example A: Traditional Analytics Using Charges as Proxy

Patient Charges: $50,000
Aggregate Cost-to-Charge Ratio: 40%
Estimated Cost of Patient Care: $20,000 (Charges×CTC Ratio)
Profit: $30,000 (Charges–Estimated Cost)

Example B: Profitability Analytics

Patient Charges: $50,000
Actual Cost of Patient Care: $15,000 (per above example)
Contracted Payment: $18,000 (per patient's insurance company contract)
Contractual Discount: $32,000 (Patient Charges–Contracted Payment)
Net Patient Revenue: $18,000 (Patient Charges–Contractual Discount)
Profit: $3,000 (Net Patient Revenue–Actual Cost of Patient Care)

The analytics engine 110, through a combination of hierarchical relationships and computational methods, may enable fast, targeted reporting capabilities aimed at uncovering key root causes of variability which negatively impact quality and profitability. The analytics engine 110 may provide a reporting construct that enables users to aggregate raw data into meaningful groupings as well as drill down from roll-up metrics into component variables and episodic data points. The analytics engine 110 may also provide a hierarchical construct enabling analysis of a myriad of population subsets based on patient demographics, physician interactions, organizational accountability, population health characteristics and disease states, and third party payer alignments. The hierarchical relationship mapping may allow for rapid meaningful drill down into deeper layers of specificity and accountability. For example, the analytics engine 110 may identify that diagnosis related group (DRG) code 476 has been trending unprofitable for the past 90 days. With that as a starting point, analytics engine 110 may provide the user with a GUI displaying a performance breakdown for that DRG by facility, by physician within each facility, and the specific patient encounter-level detail associated with each physician. By quickly being able to isolate the DRG 476 encounters by physicians and by facilities that are losing money versus those that are making money, the analytics engine 110 may provide the user with information on the differences (e.g., variances) in the administration of care to those patients—Operating Room Time, Product Selection and Price, Inpatient LOS, number of Labs and Images, etc.—that may contribute to both the total cost of care and the quality of the outcome.

The analytics engine 110 may provide robust statistical capabilities facilitating identification and relative stratifications of inlier and outlier populations based on components of cost, quality and clinical outcomes. For example, the analytics engine 110 may employ statistical techniques for determining inlier/outlier data points within a sample/population. Statistical analyses may be derivatives of existing Lean and Six Sigma methods, and the analytics engine 110 may apply these methods to the integrated LAR dataset to simultaneously provide for hospital quality and profitability performance analytics and improvement. The analytics engine 110 may thus generate a LAR that connects more accurate, inter-related data for use in analysis.

For comparison, conventional analysis may use charges as a proxy for cost and/or revenue for determining inlier and/or outlier populations. Conventional analysis is only as reliable as the proxy on which the distribution is based. So if there is high variability between the proxy value (charge) and actual value (cost and/or net revenue)—which there almost always is—that variability skews all subsequent analysis. Furthermore, by not connecting costs to net revenue for true profitability analysis, conventional analysis may cause an organization to effect change that actually has a negative impact on the organization's business. For example, a high-cost case may be identified using a traditional analytic approach, with charges as the proxy for cost/revenue, and then the organization creates a clinical protocol to change the way in which that patient is treated. The new protocol may result in fewer charges, but the new total cost-reimbursement scenario actually yields less profitability for the same clinical outcome.

The example embodiments may use statistical analysis as part of patient care. Based on statistical analysis, the analytics engine 110 may trigger alerts and may assist in treating a patient while the patient is still under a hospital's care. In an example, the analytics engine 110 may apply statistical modeling to determine when a particular process is drifting outside of a desired range or deviating from a desired treatment that may negatively affect a clinical outcome for the patient and/or result in a poor financial outcome for the hospital. The analytics engine 110 may generate the statistical model based on aggregating data received from one or more data source servers 104A-N (e.g., from a supplier, one or more hospitals, etc.).

The analytics engine 110 may process the LARs and corresponding event entries to generate a statistical model for determining how variability in patient treatment impacts clinical outcomes at the patient encounter level. The statistical model may indicate the probability of an adverse clinical outcome based on a current value for a parameter. Adverse clinical incomes may be based on length of hospital stay, infection rate, readmissions, and the like. In an example, each LAR may have a diagnosis code indicating the diagnosed ailment for a particular patient and a number of event entries. Each event entry may include a time stamp (e.g., time and date of treatment) and one or more of a procedure code, a drug identifier, a supply identifier, and the like. A procedure code may identify what treatment a patient was provided. The drug identifier may be, for example, a hospital's proprietary code for identifying a drug or an NDC of a drug given to the patient. The supply identifier may be, for example, a hospital's proprietary code for identifying a supply item or a manufacturer's code for identifying a supply item used to treat a patient.

The statistical model may also consider demographics of the patient when generating the statistical model. For example, the analytics engine 110 may generate the statistical model utilizing LARs of patients having demographics similar to the patient. Example demographic data includes age, race, ethnicity, geographic location, and the like. In an example, the analytics engine may create a statistical model for determining the likelihood of patients having a similar demographic profile as a particular patient have over a predetermined percentage chance of an adverse outcome (e.g., getting an infection). An adverse outcome may also be based on a poor financial outcome or penalty (e.g., the hospital bears the cost for treating the adverse outcome, rather than the insurance company).

In an example, a user (e.g., hospital administrator) may desire to know how variability impacts clinical outcomes. For instance, it may be known that leaving a catheter in a patient for extended periods of time may potentially lead to an infection, but data may be lacking on when to alert a clinician that a catheter has been inserted for too long. To generate the statistical model, the analytics engine 110 may search the LAR database 118 to retrieve LARs having a particular procedure code (e.g., corresponding to insertion of a catheter), or a set of procedure codes, and corresponding event entries. For example, the analytics engine 110 may search event entries in the retrieved LARs to determine when a catheter was inserted and subsequently removed. The retrieved LARs may also correspond to a particular diagnosis code. For example, a hospital administrator may desire to know the probability of infection due to catheter insertion for patients that received a coronary artery bypass graft, and thus the analytics engine 110 may retrieve LARs for patients that had a catheter inserted and received a coronary artery bypass graft. Thus, the analytics engine 110 may tailor the statistical model to any desired level of granularity.

The analytics engine 110 may process the retrieved LARs to determine whether or not an adverse clinical outcome occurred. For example, the analytics engine 110 may process the retrieved LARs to determine whether the patient subsequently developed an infection within a predetermined amount of time (e.g., 30 days). The analytics engine 110 may aggregate data from the retrieved LARs to determine the percentage of patients that had an adverse clinical outcome. For example, the analytics engine 110 may determine the percentage of patients who subsequently developed an infection at hourly increments after a catheter was inserted. The analytics engine 110 may use the percentages to create a statistical model for determining the probability of an adverse outcome. For example, the statistical model may indicate the probability of a patient developing an infection based on the length of time a catheter has been inserted. In an example, the statistical model may indicate that a patient has a 0.5% chance of getting an infection when a catheter has been inserted for 36 hours, a 1.5 percent chance of infection at 52 hours, and a 5% chance of infection at 75 hours.

The analytics engine 110 may apply the statistical model to data associated with treatment of a particular patient (e.g., a patient currently in the hospital) to determine whether treatment of the particular patient has deviated from a desired treatment. The patient's current treatment, for example, may statistically result in a poor clinical outcome for the patient and/or a poor financial outcome for the hospital. For instance, the analytics engine 110 may analyze the patient's LAR and/or ingested data for a patient to determine how long a catheter has been inserted into the patient. For example, the analytics engine 110 may process event entries and determine current values of parameters corresponding to a procedure code at issue. In an example, a procedure code may indicate that a catheter was inserted into a patient and a corresponding time stamp may indicate the time of insertion. The analytics engine 110 may determine a time difference between the current time/date and the time stamp to determine a length of time that the catheter has been inserted. The time difference may be the current value of a time parameter. The analytics engine 110 may apply the current value of the parameter in the statistical model to determine a probability of an adverse outcome. Continuing this example, the analytics engine 110 may utilize the statistical model to determine the probability that the patient may develop an infection based on how long the catheter has been inserted.

In some instances, the analytics engine 110 may cause treatment to be administered to the patient. Treatment may be administered via alerting a clinician (e.g., nurse, doctor, etc.) and/or automatically. In an example, the analytics engine 110 may trigger an alert when the statistical model indicates that the probability of an adverse outcome exceeds a threshold (e.g., 75%). The analytics engine 110 may electronically communicate the alert via network 106 to a device of a clinician (e.g., a doctor, a nurse, etc.), and may also communicate the alert to a device of a hospital administrator (or other third party). Examples of devices include a mobile phone, a smart phone, a computer, a pager, and the like. The alert may also identify the problem and provide a description of the recommended treatment (e.g., remove the catheter).

In some instances, a device associated with the clinician may or may not be in an active state. For example, a clinician's device may be in a sleep mode to conserve battery life. Because an alert may be time sensitive, the alert may cause the clinician's device to exit the sleep mode and enter an active state. In some examples, the clinician's device may, in response to receiving the alert, perform one or more of the following: display the alert on a graphical user interface (GUI), display a probability of the adverse outcome on the GUI, display a recommended treatment on the GUI, emit a sound, prompt a clinician to send an acknowledgment message via a device in reply to the alert via the network 106, and/or establish a network connection for receiving additional data from the analytics engine 110 about the alert. The analytics engine 110 may also monitor for the acknowledgement and may communicate the alert to other clinician devices if an acknowledgement is not received within a predetermined amount of time. For example, the analytics engine 110 may process a hierarchy indicating in what order clinician devices are to be contacted, and proceed up the hierarchy if an acknowledgment is not received from a lower level clinician's device. In an example, the hierarchy may specify to first contact a nurse, then a head nurse, then a doctor, and then a head doctor. The analytics engine 110 may respectively send an alert to each clinician's device until at least one of the devices in the hierarchy responds to the alert with an acknowledgment.

In other examples, the healthcare provider may preapprove certain treatments to be automatically given to a patient in certain situations. For example, a healthcare provider may approve prophylactically administering an antibiotic when the probability of developing an infection exceeds a predetermined threshold. In an example, the analytics engine 110 may determine whether a treatment can be administered automatically in response to the triggered alert. For example, the analytics engine 110 may process the LAR to look for a procedure code and time stamp to determine if the patient is currently receiving intravenous therapy (IV) and whether a networked, automated, drug delivery pump is connected to the IV. If yes, the analytics engine 110 may communicate with the drug delivery pump via network 106 to determine if the delivery pump is loaded with an antibiotic pre-approved by the healthcare provider. If yes, the analytics engine 110 may instruct the drug delivery pump to administer the antibiotic to the patient via the IV. If analytics engine 110 determines that the patient is not attached to an IV, the analytics engine 110 may communicate via network 106 with a robotic mobile dispensary that circulates through a building of the healthcare provider to cause the mobile dispensary to proceed to the patient's room to deliver the antibiotic (e.g., in pill form) to the patient.

After triggering the alert, the analytics engine 110 may collect data from one or more data feeds input associated with the patient indicating whether the clinician followed the recommendation in the alert. The analytics engine 110 may also collect data from one or more data feeds based on the patient's clinical outcome (e.g., whether patient got an infection) subsequent to sending the alert. Using this data, the analytics engine 110 may update the statistical model based on whether the practitioner followed the recommendation and the clinical outcome to adjust when alerts are sent in the future. For example, the analytics engine 110 may adjust the statistical model and the corresponding probability that a patient has an adverse outcome based on recorded instances of actual adverse outcomes (e.g., adjust probability of getting an infection based on recorded instances of actual infection rates). The adjustment may take into account the demographic profile of the patient.

The analytics engine 110 may also use statistical analysis to generate product/drug recommendations for healthcare practitioners based on a probability of an adverse outcome. In an example, a practitioner may have preferred medical supplies and drugs, but these preferences may not result in a better clinical outcome for patients and/or a better financial outcome for the hospital. Prior to performing a medical procedure, the practitioner may electronically submit a preference card identifying proposed medical supplies and/or drugs to be used during the procedure. The analytics engine 110 may apply a statistical model to assess clinical and financial impact of the practitioner's proposal based on the probability of an adverse outcome. The analytics engine 110 may attempt to identify other less expensive medical supplies and/or drugs that have statistically resulted in a similar or better clinical outcome and resulted in a better financial outcome. For example, the analytics engine 110 may retrieve LARs having the same diagnosis code as the one specified in the practitioner's preference card. The analytics engine 110 may categorize the LARs into groups based on what drugs and/or supplies were used to treat patients having the same diagnosis code. For example, the analytics engine 110 may determine that patients receiving knee replacements received replacement knees from three different manufacturers. The analytics engine 110 may process the LARs for each group to determine the percentage of patients that had an adverse outcome (e.g., 15% of patients that received a first replacement knee had an adverse outcome, 25% of patients that received a second replacement knee had an adverse outcome, and 7% of patients that received a third replacement knee had an adverse outcome). The analytics engine 110 may also determine a statistical measure of the total cost of care for patients in each group. Examples of a statistical measure are an average, median, standard deviation, minimum, maximum, and the like. In an example, the analytics engine 110 may apply the statistical model to determine an average total cost of care and probability of an adverse outcome based on data provided in the preference card. The analytics engine 110 may trigger an alert if the statistical measure for the practitioner's selected drug/supply combination is worse than a statistical measure for a different drug/supply combination and/or has a probability of an adverse outcome that exceeds at least one other drug/supply combination. For example, a surgeon may have selected a first replacement knee, and the analytics engine 110 may apply the statistical model to determine that a second replacement knee has a lower average total cost of care and a lower probability of an adverse outcome. In some instances, the analytics engine 110 may weight the statistical measure and probability of an adverse outcome for determining which drug/supply combination to recommend. For example, the analytics engine 110 may weight the probability of an adverse outcome higher than the average total cost of care.

In some examples, if the analytics engine 110 identifies an improvement in at least one of clinical and financial outcomes, and a similar outcome in the other, the analytics engine 110 may electronically communicate an alert to a clinician recommending consideration of an alternate medical supply and/or drug. A similar outcome may be a slightly worse outcome in some instances, or may be an equivalent or better outcome. The analytics engine 110 may collect data input by the clinician or other user on whether the clinician followed the recommendation. The analytics engine 110 may also update the statistical model to adjust when alerts are sent in the future. For example, the analytics engine 110 may determine that medical supplies and/or drugs initially thought to perform statistically similarly actually perform better and/or worse. If better, the analytics engine 110 may recommend those medical supplies and/or drugs, and, if worse, the analytics engine may not recommend them.

Figure 5:
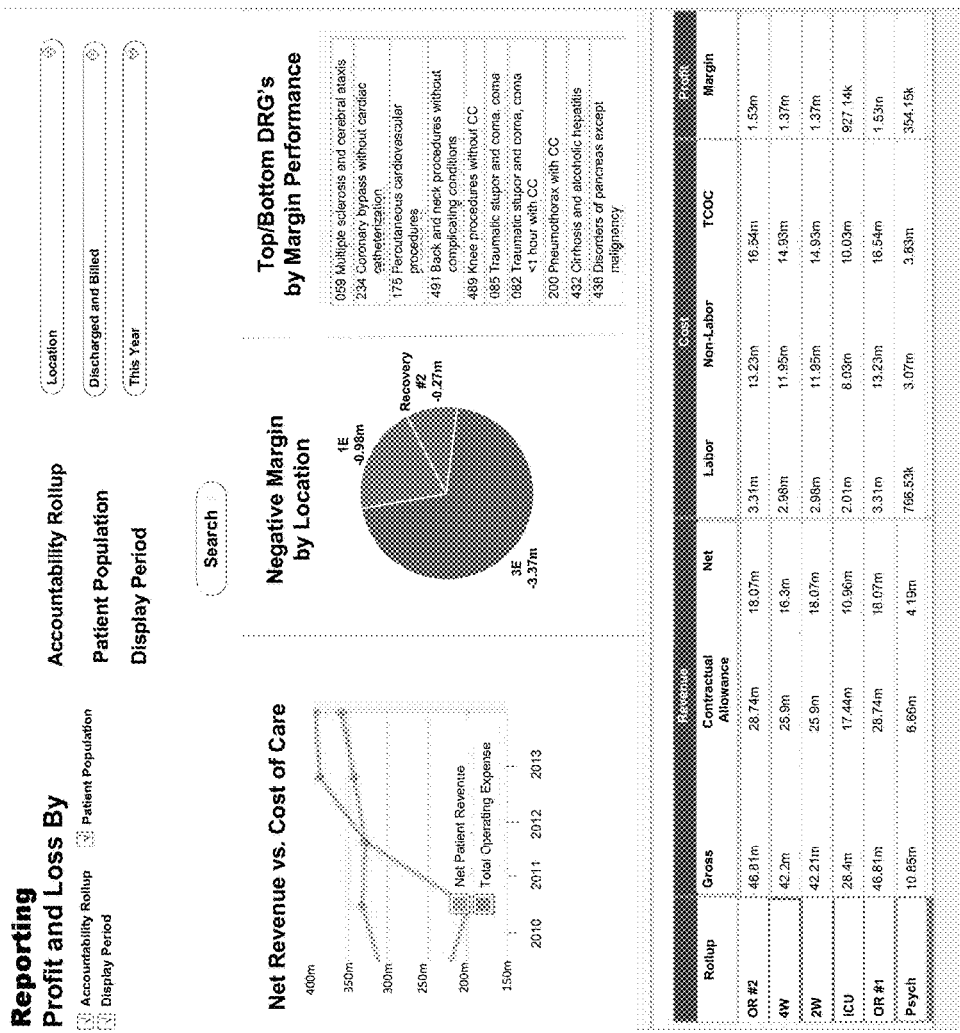

FIG. 5 illustrates an example graphical user interface (GUI) for automated profitability opportunity identification and root cause analysis configurable by patient population subsets in accordance with example embodiments. As depicted, the GUI may present information on profit and loss based on categories selectable by a user. Example categories may include accountability rollup, patient population, and display period. Accountability rollup may permit a user to select a particular location within a hospital (e.g., ER, ICU, etc.) for analysis. Patient population may permit selection of patients based on one or more of demographics, third party payer alignment, and clinical conditions (e.g., diabetes, core measures, etc.). Display period may permit selection of a desired period of time or time range (e.g., 2014). The GUI may display a line graph depicting net revenue versus cost of care for the selected time period (e.g., 2010-2013). The GUI may also display a chart (e.g., pie chart) listing negative margin by location within the hospital. The GUI may further identify top/bottom diagnosis related group's (DRGs) by margin performance. The GUI may include a table listing financial data for revenue, cost, and profit for one or more locations within the hospital. Revenue data may include, by location within the hospital, gross revenue data, contractual allowance, and net income data. Cost data may include, by location within the hospital, labor costs, non-labor costs, and total cost of care (TCOC). Profit data may include, by location within the hospital, an operating margin.

Referring again to FIG. 2, in the bottom right branch the analytics engine 110 may integrate supplier and payer contract details into actual cost, utilization, and revenue performance datasets to maximize hospital financial performance within the existing contracting framework. Within the existing contracting framework, benefit occurs when the hospital is able to continuously monitor vendor/GPO contract compliance in order to achieve better pricing tiers (e.g., bigger discounts), attain volume or market-share based rebates. Additional benefit may come from rapid identification of price discrepancies that may be able to be recaptured. For example, a contracted item may be purchased, but the hospital buyer fails to reference the contract ID# in the purchase, and therefore an inappropriate higher price is applied to the invoice. By identifying these overcharges, the hospital could submit to the vendor for a partial refund (the difference between the actual price paid and the contracted price). The same concept holds true on third party payer contracts. Insurance companies may issue underpayments on accounts, but the remaining balances are subsequently written off in error as contractual allowances. By automating the analysis of payments against contractual obligations, the analytics engine 100 may identify underpayments more quickly and easily, and provide for collecting additional balances more efficiently. In some cases, underpayments may total to hundreds of thousands of dollars for one hospital under a single insurance contract.

The analytics engine 110 may further identify opportunities for contract evolution and enable scenario-based modeling for a variety of risk-sharing contract structures. On the supply side, examples of opportunities the analytics engine 110 may identify include:

Contract Consolidations—For example, a hospital may have multiple contracts for the same product or service at different price points across departments of facilities. The analytics engine 110 may identify the multiple contracts and recommend that they be combined into a single enterprise level master agreement would capture additional economies of scale resulting in a lower total price across the hospital.

Volume shifting—The analytics engine 110 may identify disparities between contracts or between pricing for substitutable products and may provide incentives for the hospital to shift volume from one vendor to another or from one contract to another.

Sub-optimal pricing—The analytics engine 110 may perform comparative market analytics to identify opportunities where current contract pricing is sub-optimal and significant savings could be achieved through re-negotiation or RFP.

On the revenue side, examples of opportunities the analytics engine 110 may identify include risk-based opportunities related to shared-accountability and/or population health management opportunities. In this framework, the analytics engine 110 may identify specific patient population subsets in which the volume, quality and costs of care indicate that the transition from fee-for-service (FFS) contracting to value-based contracting (VBC) could be advantageous. Fee-for-service means the hospital is paid a set amount based on the volume of care it provides, regardless of the outcome of the care. Value-based contracting means that the hospital is incentivized by the payer to provide high quality care at a low cost, and subsequently shares in a percentage of the savings generated. Value-based contracting can take on many forms, but may involve lower up-front payments coupled with financial incentives for effective quality and cost management of a patient population in the form of bonus payments, shared savings payments, and directed market share (a practice by which an insurance company structures its health plans to intentionally steer enrolled patients toward a specific high quality, low cost healthcare provider.)

For example, if a hospital consistently performs hip replacement services at a low cost, with a low length of stay (LOS), and a low rate of surgical site infections and revisions, the analytics engine 110 may identify an opportunity to enter into a value-based contract (VBC) with the subset of its contracted payers that have high volumes of hip replacement candidates. By analyzing both the hospital's quality and cost performance for a procedure, DRG, or clinical population against the volume, demographic, and contract details of their payer network, the analytics engine 110 can begin to automate the identification of potential payer contracting opportunities to accelerate the shift from fee for service (FFS) to VBC.

In another example, the analytics engine 110 may leverage the supply formulary matrix to identify margin interdependencies between supply contracting and revenue contracting terms for chargeable implantable medical devices and drugs. In many instances, these costly devices and drugs have an associated reimbursement construct, commonly referred to as a "carve-out", that is captured in a third payer contract. Often, these constructs allow the hospital a certain markup on the cost of the device and then attach a predetermined discount rate for the insurance company. When hospitals undertake initiatives to reduce the contracted price of chargeable implantable devices without first taking into account the net revenue impact, they expose themselves to risk that the magnitude of the reduction in revenue that corresponds to the new lower device pricing will exceed that of the savings itself, thus resulting in margin erosion. Through its ability to link product pricing information to third party payer contract terms, analytics engine 110 decisions may support analytics to supply chain and finance during supply and payer contract negotiations. The following table illustrates the potential negative margin impact that this type of a scenario currently produces for hospitals:

TABLE

Potential Negative Margin Impact of Chargeable Supply Cost Reduction

|  | Scenario #1 | Scenario #2 |
|---|---|---|
| Supply Amount Billed to Payor (Contracted 5x markup) | $5,000 | $2,500 |
| Reimbursement to Hospital (Contracted 50% of Charge) | $2,500 | $1,250 |
| Cost of Implantable Device | (−$1,000) | (−$500) |
| Total Income for Hospital | $1,500 | $750 |
| Margin Impact of $500 Unit Cost Reduction | (−$750) | |

As illustrated in the example above, a negotiated unit price reduction for a chargeable supply can yield an unintended negative profit margin impact due to the structure of the organization's managed care contracts—the magnitude of which may exceed the positive margin benefit provided by the front-end supply savings. Currently, hospitals are either unaware of this relationship, unable to provide visibility into it, or have to manually run these types of financial models.

In another example, the analytics engine 110 may identify underlying causes of variability that directly lead to adverse outcomes along with corresponding actionable improvement options. In addition, variability and subsequent actionable improvement steps are identified related to both supply and payer contracting structures versus actual performance against contract terms. For example, the analytics engine 110 may identify existing variance of actual purchasing and reimbursement activity against current contracts to identify non-compliance, over-payments to suppliers, and underpayments from insurance companies. For instance, the analytics engine 110 may identify where the hospital is failing to leverage its existing contracts (e.g., by purchasing from someone else outside of an existing contract at a higher price). In another example, the analytics engine 110 may identify when purchase volume may be leveraged to obtain a lower purchase price. For instance, the analytics engine 110 may determine a total quantity of a medical supply purchased by a hospital from multiple suppliers. The analytics engine 110 may identify any volume-based discounts which the hospital may qualify for under the existing contracts to find which supplier offers a lowest price. Once identified, the analytics engine 110 may provide a product ordering interface that limits ordering of the medical supply only from the lowest price supplier. The analytics engine 110 may further change and/or cancel existing orders to instead only use the lowest price supplier. Further, the analytics engine 110 may automatically search the internet for other suppliers in search of lower advertised prices, and may automatically order from those suppliers instead.

Moreover, the analytics engine 110 may identify diagnosis and procedural subsets with stable process outcomes and favorable profitability characteristics and use suggestive analytics to highlight potentially favorable contracting opportunities and alternative models. In an example, the analytics engine 110 may make recommendations on where a hospital should take on a risk sharing agreement with an insurance provider. For instance, the analytics engine 110 may identify procedures where the hospital has favorable outcomes for its patients, and may be willing to take on a risk sharing agreement.

Figure 6:
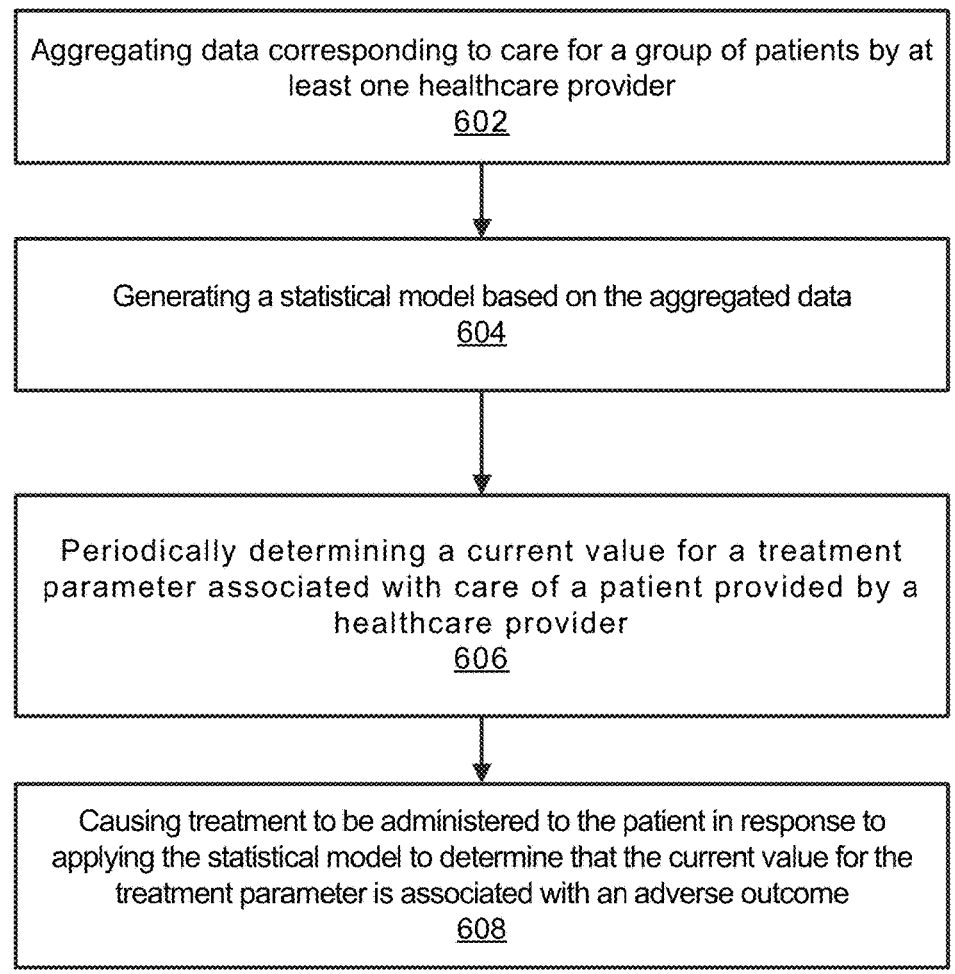
FIG. 6 illustrates a flow diagram of a method in accordance with example embodiments.

FIG. 6 illustrates a flow diagram of a method in accordance with example embodiments. The flow diagram may be implemented by a system or apparatus, such as, for example, analytics engine 110 of analysis server 102. Each of the blocks shown in the flow diagram may be repeated one or more times, one or more of the blocks may be modified, and one or more of the blocks may be omitted. The method may be stored on a non-transitory computer readable medium as computer executable instructions. The computer executable instructions, when executed by at least one processor, may cause the at least one processor, at least one computer, or other device to perform the blocks as steps of a method one or more times. The flow diagram may begin at block 802.

In block 602, the method may include aggregating data corresponding to care for a group of patients by at least one healthcare provider. For example, an analytics engine 110 of the analysis server 108, may process patient LARs to aggregate data corresponding to care for a group of patients by at least one healthcare provider. In an example, data may be aggregated on a particular procedure or treatment patients received and a corresponding clinical outcome. The aggregated data may be based on treatments provided by a particular healthcare provider and other providers (e.g., peer healthcare providers)

In block 604, the method may include generating a statistical model based on the aggregated data. In an example, the analytics engine 110 may process patient LARs to generate a statistical model for determining a probability of an adverse outcome for a particular treatment parameter. The analytics engine 110 may process the LARs to determine in which instances an unfavorable clinical outcome occurred. For example, the analytics engine 110 may determine how long a catheter was inserted into each patient and whether or not each patient developed an infection. The analytics engine 110 may generate a statistical model that indicates the probability that a patient will develop an infection based on how long a catheter has been inserted. In another example, the statistical model may indicate a probability that a patient will be readmitted for any reason based on how long a catheter has been inserted.

In block 606, the method may include periodically determining a current value for a treatment parameter associated with care of a patient provided by a healthcare provider. In an example, the analytics engine 110 may determine a time/date stamp associated with when a procedure was performed, and periodically determine a current value for a treatment parameter based on the time/date stamp. For example, the analytics engine 110 may periodically determine the amount of time that a catheter has been inserted into a patient.

In block 608, the method may include causing treatment to be administered to the particular patient in response to applying the statistical model to determine that the current value for the treatment parameter is associated with an adverse outcome. In an example, the analytics engine 110 may apply the statistical model to determine whether the current value is associated with an adverse outcome. Continuing the example above, the analytics engine 110 may determine how long a catheter has been inserted into a patient (e.g., 79 hours, 3 minutes, and 42 second). The analytics engine 110 may utilize the statistical model to determine a probability of an adverse clinical outcome based on the current value for the treatment parameter. The analytics engine 110 may compare the probability to a threshold. If above the threshold, the analytics engine 110 may cause treatment to be administered to a patient. For example, the analytics engine 110 may cause treatment to be administered to a patient by electronically communicating an alert to a clinician for administering the treatment. In another example, the analytics engine 110 may automatically administer treatment to a patient. To do so, the analytics engine 110 may detect that a patient has an inserted IV and that a networked drug delivery pump is connected to the IV. The analytics engine 110 may communicate an instruction to the drug delivery pump via a computer network to dispense a predetermined amount of the drug to the patient via the IV. For example, the drug delivery pump may prophylactically dispense an antibiotic in an attempt to prevent the patient from developing an infection due to the amount of time that a catheter has been inserted into the patient.

The method of FIG. 6 may end, may repeat one or more times, or may return to any of the preceding blocks.

Advantageously, the example embodiments may provide technical solutions to technical challenges. Existing systems of healthcare providers maintain clinical and financial data, but fail to leverage this data to improve clinical and financial outcomes. The example embodiments provide technical solutions to these technical challenges by creating a statistical model from longitudinal patient administration records (LARs) created at the patient encounter level. The statistical model may be used to determine a probability of an adverse outcome and to cause administration of treatment to a patient based on the probability. Moreover, the example embodiments may provide outputs that may reduce non-value added variability resulting in delivery of improved and more predictable operational and clinical outcomes, at a lower total cost, which consequently yield improved profitability for the organization. Further, the example embodiments may integrate disparate data and create LARs that provide insight into profitability, within the context of clinical utilization and outcomes. The example embodiments may thus connect work being done and outcomes produced by the work directly to the magnitude of financial performance those clinical activities produce.

The example embodiments may be implemented on computers and servers such as, for example, general purpose computers that may have, among other elements, a microprocessor (such as from the Intel Corporation, AMD or Motorola); volatile and non-volatile memory; one or more mass storage devices (i.e., a hard drive); various user input devices, such as a mouse, a keyboard, or a microphone; and a video display system. The computers and servers in FIG. 1 may be running on any one of many operating systems including, but not limited to WINDOWS, UNIX, LINUX, MAC OS, or Windows (XP, VISTA, etc.). It is contemplated, however, that any suitable operating system may be used for the present invention. The computers and servers in FIG. 1 may be a cluster of web servers, which may each be LINUX based and supported by a load balancer that decides which of the cluster of web servers should process a request based upon the current request-load of the available server(s).

The computers and servers may be connected via networks, including the Internet, WAN, LAN, Wi-Fi, other computer networks (now known or invented in the future), and/or any combination of the foregoing. It should be understood by those of ordinary skill in the art having the present specification, drawings, and claims before them that networks may connect the various components over any combination of wired and wireless conduits, including copper, fiber optic, microwaves, and other forms of radio frequency, electrical and/or optical communication techniques. It should also be understood that any network may be connected to any other network in a different manner. The interconnections between computers and servers in system 100 are examples. Any device may communicate with any other device via one or more networks.

The example embodiments may include additional devices and networks beyond those disclosed. Further, the functionality described as being performed by one device may be distributed and performed by two or more devices. Multiple devices may also be combined into a single device, which may perform the functionality of the combined devices.

The various participants and elements described herein may operate one or more computer apparatuses to facilitate the functions described herein. Any of the elements in the above-described Figures, including any servers, user terminals, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++, or Perl using, for example, conventional or object-oriented techniques.

The software code may be stored as a series of instructions or commands on a non-transitory computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus and may be present on or within different computational apparatuses within a system or network.

It may be understood that the present invention as described above can be implemented in the form of control logic using computer software in a modular or integrated manner. Based on the disclosure and teachings provided herein, a person of ordinary skill in the art may know and appreciate other ways and/or methods to implement the present invention using hardware, software, or a combination of hardware and software.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention. A recitation of "a", "an" or "the" is intended to mean "one or more" unless specifically indicated to the contrary. Recitation of "and/or" is intended to represent the most inclusive sense of the term unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the principles of one or more inventions and is not intended to limit any one of the inventions to the embodiments illustrated. [87] The present disclosure provides a solution to the long-felt need described above. In particular, systems and methods described herein may be configured to improve management of healthcare service providers. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

What is claimed:

1. An apparatus comprising:
   at least one processor; and
   at least one memory storing computer executable instructions that, when executed, cause the at least one processor at least to perform:
      retrieving a plurality of patient and physician longitudinal administrative records (LARs) that each correspond to a member of a first group of patients and a group of physicians, respectively;
      aggregating, from the retrieved LARs, data corresponding to an episode of care that is common for each member of the first group of patients and the group of physicians by multiple healthcare providers;
      retrieving a drug and supply formulary matrix for the episode of care, the drug and supply formulary matrix including supply data and acquisition cost data for the episode of care;
      allocating the supply data and the acquisition cost data to each patient of the first group of patients for the episode of care;
      generating a statistical model based on the aggregated data;
      periodically determining a current value for the episode of care for the LARs provided by each of the plurality of healthcare providers; and
      causing treatment to be administered for the episode of care to a second group of patients in response to applying the statistical model to determine that the current value for the episode of care is associated with an adverse outcome.

2. The apparatus of claim 1, wherein the applying of the statistical model determines a probability that the adverse outcome will occur for the current value, wherein the causing of the treatment to be administered is in response to determining that the probability exceeds a threshold.

3. The apparatus of claim 1, wherein the adverse outcome is an infection or a readmission.

4. The apparatus of claim 1, wherein the causing of the treatment to be administered to the patient comprises electronically communicating an alert to a device for prompting a clinician to administer the treatment.

5. The apparatus of claim 4, wherein the alert causes the device to display the current value for the episode of care, a probability of the adverse outcome, and a description of the treatment.

6. The apparatus of claim 4, wherein the alert causes the device to exit a sleep mode and establish a network connection for receiving data.

7. The apparatus of claim 1, wherein the causing of the treatment to be administered to the patient comprises controlling a drug delivery pump to automatically dispense a drug to the patient.

8. A computer-implemented method comprising:
   retrieving, by an ingestion engine comprising at least one processor and at least one memory, a plurality of patient and physician longitudinal administrative records (LARs) that each correspond to a member of a first group of patients and a group of physicians, respectively;
   aggregating, by an analytics engine comprising at least one processor and at least one memory storing computer executable instructions, from the retrieved LARs, data corresponding to an episode of care that is common for each member of the first group of patients and the group of physicians by multiple healthcare providers;
   retrieving, by the ingestion engine, a drug and supply formulary matrix for the episode of care, the drug and supply formulary matrix including supply data and acquisition cost data for the episode of care;
   allocating, by the ingestion engine, the supply data and the acquisition cost data to each patient of the first group of patients for the episode of care;
   generating, by the analytics engine, a statistical model based on the aggregated data;
   periodically determining, by the analytics engine, a current value for the episode of care for the LARs provided by each of the plurality of healthcare providers; and
   causing, by the analytics engine, treatment to be administered for the episode of care to a second group of patients in response to applying the statistical model to determine that the current value for the episode of care is associated with an adverse outcome.

9. The method of claim 8, wherein the applying of the statistical model determines a probability that the adverse outcome will occur for the current value, wherein the causing of the treatment to be administered is in response to determining that the probability exceeds a threshold.

10. The method of claim 8, wherein the adverse outcome is an infection or a readmission.

11. The method of claim 8, wherein the causing of the treatment to be administered to the patient comprises electronically communicating an alert to a device for prompting a clinician to administer the treatment.

12. The method of claim 11, wherein the alert causes the device to display the current value for the episode of care, a probability of the adverse outcome, and a description of the treatment.

13. The method of claim 11, wherein the alert causes the device to exit a sleep mode and establish a network connection for receiving data.

14. The method of claim 8, wherein the causing of the treatment to be administered to the patient comprises controlling a drug delivery pump to automatically dispense a drug to the patient.

15. A non-transitory computer readable medium storing instructions that, when executed, cause at least one processor to perform at least:

retrieving a plurality of patient and physician longitudinal administrative records (LARs) that each correspond to a member of a first group of patients and a group of physicians, respectively;

aggregating, from the retrieved LARs, data corresponding to an episode of care that is common for each member of the first group of patients and the group of physicians by multiple healthcare providers;

retrieving a drug and supply formulary matrix for the episode of care, the drug and supply formulary matrix including supply data and acquisition cost data for the episode of care;

allocating the supply data and the acquisition cost data to each patient of the first group of patients for the episode of care;

generating a statistical model based on the aggregated data;

periodically determining a current value for the episode of care for the LARs provided by each of the plurality of healthcare providers; and causing treatment to be administered for the episode of care to a second group of patients in response to applying the statistical model to determine that the current value for the episode of care is associated with an adverse outcome.

16. The computer readable medium of claim 15, wherein the applying of the statistical model determines a probability that the adverse outcome will occur for the current value, wherein the causing of the treatment to be administered is in response to determining that the probability exceeds a threshold.

17. The computer readable medium of claim 15, wherein the causing of the treatment to be administered to the patient comprises electronically communicating an alert to a device for prompting a clinician to administer the treatment.

18. The computer readable medium of claim 17, wherein the alert causes the device to display the current value for the episode of care, a probability of the adverse outcome, and a description of the treatment.

19. The computer readable medium of claim 17, wherein the alert causes the device to exit a sleep mode and establish a network connection for receiving data.

20. The computer readable medium of claim 15, wherein the causing of the treatment to be administered to the patient comprises controlling a drug delivery pump to automatically dispense a drug to the patient.

* * * * *